(12) United States Patent
Kim et al.

(10) Patent No.: US 10,226,190 B2
(45) Date of Patent: Mar. 12, 2019

(54) DIAGNOSTIC MEASURING DEVICE

(75) Inventors: Yoon Ok Kim, Schwerte (DE); Ok Kyung Cho, Schwerte (DE)

(73) Assignee: Ingo FLORE, Dortmund (DE)

( * ) Notice: Subject to any disclaimer, the term of this patent is extended or adjusted under 35 U.S.C. 154(b) by 0 days.

(21) Appl. No.: 13/138,555

(22) PCT Filed: Mar. 5, 2010

(86) PCT No.: PCT/EP2010/001374
§ 371 (c)(1),
(2), (4) Date: Sep. 28, 2011

(87) PCT Pub. No.: WO2010/099969
PCT Pub. Date: Sep. 10, 2010

(65) Prior Publication Data
US 2012/0016210 A1    Jan. 19, 2012

(30) Foreign Application Priority Data

Mar. 5, 2009   (DE) .................. 10 2009 011 381

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0402* (2013.01); *A61B 5/14552* (2013.01);
(Continued)

(58) Field of Classification Search
CPC ..... H04B 7/0695; H04B 7/088; H04W 72/00; H04W 72/04; H04W 72/046;
(Continued)

(56) References Cited

U.S. PATENT DOCUMENTS 3,229,686 A   1/1966  Edmark, Jr.
3,805,795 A   4/1974  Denniston et al.
(Continued)

FOREIGN PATENT DOCUMENTS

DE    35 33 912    4/1987
DE   195 19 125   11/1996
(Continued)

OTHER PUBLICATIONS

International Search Report of PCT/EP2010/001374, dated Jul. 6, 2010.
(Continued)

*Primary Examiner* — Carolyn Pehlke
(74) *Attorney, Agent, or Firm* — Collard & Roe, P.C.

(57) ABSTRACT

The invention relates to a diagnostic measuring device for non-invasively collecting at least one physiological parameter of body tissue by way of an optical measuring unit (100), comprising at least one source of radiation (4) for irradiating the body tissue to be examined, and at least one radiation sensor (5) for detecting the radiation scattered and/or transmitted by the body tissue. The invention proposes the arrangement of the at least one source of radiation (4, 702) within a hollow reflector (701).

23 Claims, 5 Drawing Sheets (51) Int. Cl.
    *A61B 5/1455* (2006.01)
    *A61B 5/0402* (2006.01)
    *A61B 5/053* (2006.01)
(52) U.S. Cl.
    CPC .......... *A61B 5/6826* (2013.01); *A61B 5/6838* (2013.01); *A61B 5/6843* (2013.01); *A61B 5/0006* (2013.01); *A61B 5/0008* (2013.01); *A61B 5/0017* (2013.01); *A61B 5/053* (2013.01)
(58) Field of Classification Search
    CPC .............. A61B 5/02416; A61B 5/0402; A61B 5/14552; A61B 5/6826; A61B 5/6838; A61B 5/6843
    See application file for complete search history.

(56) References Cited

U.S. PATENT DOCUMENTS

| | | | |
|---|---|---|---|
| 3,958,560 A | 5/1976 | March | |
| 4,310,246 A * | 1/1982 | Blazek | G01J 1/04 250/228 |
| 4,610,254 A | 9/1986 | Morgan et al. | |
| 4,907,596 A | 3/1990 | Schmid et al. | |
| 4,911,167 A | 3/1990 | Corenman et al. | |
| 4,928,014 A | 5/1990 | Rosenthal | |
| 4,934,382 A | 6/1990 | Barone, Jr. | |
| 4,938,218 A * | 7/1990 | Goodman et al. | 600/338 |
| 4,960,126 A | 10/1990 | Conlon et al. | |
| 5,153,426 A * | 10/1992 | Konrad et al. | 250/227.24 |
| 5,191,891 A | 3/1993 | Righter | |
| 5,237,178 A | 8/1993 | Rosenthal et al. | |
| 5,259,381 A | 11/1993 | Cheung et al. | |
| 5,309,916 A | 5/1994 | Hatschek | |
| 5,353,790 A * | 10/1994 | Jacques et al. | 600/315 |
| 5,431,170 A | 7/1995 | Mathews | |
| 5,515,847 A | 5/1996 | Braig et al. | |
| 5,676,143 A | 10/1997 | Simonsen et al. | |
| 5,682,902 A | 11/1997 | Herleikson | |
| 5,741,211 A | 4/1998 | Renirie et al. | |
| 5,771,891 A | 6/1998 | Gozani | |
| 5,795,305 A | 8/1998 | Cho et al. | |
| 5,924,996 A | 7/1999 | Cho et al. | |
| 6,041,247 A | 3/2000 | Weckstrom et al. | |
| 6,128,518 A | 10/2000 | Billings et al. | |
| 6,159,147 A | 12/2000 | Lichter et al. | |
| 6,190,325 B1 | 2/2001 | Narimatsu | |
| 6,230,035 B1 | 5/2001 | Aoyagi et al. | |
| 6,289,230 B1 | 9/2001 | Chaiken et al. | |
| 6,331,162 B1 | 12/2001 | Mitchell | |
| 6,424,413 B1 * | 7/2002 | Weber | G01J 3/0251 250/228 |
| 6,714,814 B2 | 3/2004 | Yamada et al. | |
| 6,763,256 B2 | 7/2004 | Kimball et al. | |
| 6,790,178 B1 * | 9/2004 | Mault et al. | 600/300 |
| 6,819,950 B2 | 11/2004 | Mills | |
| 6,873,865 B2 | 3/2005 | Steuer et al. | |
| 7,215,991 B2 | 5/2007 | Besson et al. | |
| 8,046,059 B2 | 10/2011 | Cho et al. | |
| 2001/0012916 A1 | 8/2001 | Deuter | |
| 2002/0087087 A1 | 7/2002 | Oka et al. | |
| 2002/0183624 A1 * | 12/2002 | Rowe | A61B 5/117 600/476 |
| 2003/0009111 A1 | 1/2003 | Cory et al. | |
| 2003/0036685 A1 * | 2/2003 | Goodman | 600/300 |
| 2003/0055324 A1 | 3/2003 | Wasserman | |
| 2003/0109901 A1 | 6/2003 | Greatbatch | |
| 2004/0034293 A1 | 2/2004 | Kimball | |
| 2004/0116784 A1 | 6/2004 | Gavish | |
| 2004/0122336 A1 | 6/2004 | Jang et al. | |
| 2004/0152957 A1 * | 8/2004 | Stivoric et al. | 600/300 |
| 2004/0162493 A1 | 8/2004 | Mills | |
| 2004/0181132 A1 | 9/2004 | Rosenthal | |
| 2004/0225209 A1 | 11/2004 | Cho | |
| 2004/0260165 A1 | 12/2004 | Cho et al. | |
| 2005/0013999 A1 | 1/2005 | Wakefield et al. | |
| 2005/0014999 A1 | 1/2005 | Rahe-Meyer | |
| 2005/0020936 A1 | 1/2005 | Lin | |
| 2005/0033127 A1 * | 2/2005 | Ciurczak | A61B 5/14532 600/316 |
| 2005/0078533 A1 | 4/2005 | Vyshedskiy et al. | |
| 2005/0131282 A1 * | 6/2005 | Brodnick et al. | 600/323 |
| 2005/0177062 A1 | 8/2005 | Skrabal et al. | |
| 2005/0192488 A1 * | 9/2005 | Bryenton | A61B 5/02055 600/301 |
| 2005/0261594 A1 * | 11/2005 | Banet | 600/485 |
| 2006/0009697 A1 | 1/2006 | Banet et al. | |
| 2006/0129040 A1 | 6/2006 | Fine et al. | |
| 2006/0135857 A1 | 6/2006 | Ho et al. | |
| 2006/0155193 A1 | 7/2006 | Leonardi et al. | |
| 2007/0038048 A1 | 2/2007 | Gerder | |
| 2007/0073178 A1 | 3/2007 | Browning et al. | |
| 2007/0093717 A1 * | 4/2007 | Nagar | A61B 5/0095 600/438 |
| 2007/0106139 A1 | 5/2007 | Nagata et al. | |
| 2007/0265533 A1 | 11/2007 | Tran | |
| 2008/0146892 A1 | 6/2008 | LeBoeuf et al. | |
| 2008/0200823 A1 | 8/2008 | Cho et al. | |
| 2008/0275317 A1 | 11/2008 | Cho et al. | |
| 2010/0004517 A1 | 1/2010 | Bryenton et al. | |
| 2010/0056880 A1 * | 3/2010 | Cho et al. | 600/301 |
| 2012/0016210 A1 * | 1/2012 | Kim et al. | 600/301 |

FOREIGN PATENT DOCUMENTS

| | | |
|---|---|---|
| DE | 298 11 049 | 12/1998 |
| DE | 20 2005 001 894 | 5/2005 |
| EP | 1 317 902 | 6/2003 |
| EP | 1 407 713 | 4/2004 |
| EP | 1491134 | 12/2004 |
| WO | WO 90/04352 | 5/1990 |
| WO | WO 96/01585 | 1/1996 |
| WO | 99/62399 | 12/1999 |
| WO | 00/69328 | 11/2000 |
| WO | WO 01/65810 | 9/2001 |
| WO | WO 2005/048831 | 6/2005 |
| WO | WO 2005/077260 | 8/2005 |
| WO | WO 2006/099988 | 9/2006 |
| WO | WO 2007/017266 | 2/2007 |
| WO | WO 2008/061788 | 5/2008 |
| WO | WO 2008061788 A1 * | 5/2008 ............... A61B 5/00 |

OTHER PUBLICATIONS

Meir Nitzan, Boris Khanokh, "Infrared Radiometry of Thermally Insulated Skin for the Assessment of Skin Blood Flow," Optical Engineering 33, 1994, No. 9, pp. 2953-2956. (Spec, p. 12).
Cho et al., "Noninvasive Measurement of Glucose by Metabolic Heat Conformation Method," Clinical Chemistry, International Journal of Laboratory Medicine and Molecular Dianostics, 2004, vol. 50, No. 10, pp. 1894-1898.
Turner et al., "Effect of dried garlic powder tablets on postprandial increase in pulse wave velocity after a fatty meal: preliminary observations," Scandinavian Journal of Nutrition, 2005, vol. 49, pp. 21-26. XP-008079156.
Lepretre et al., "Effect of Exercise Intensity on Relationship between VO2max and Cardiac Output," Official Journal of the American College of Sports Medicine, 2004, pp. 1357-1363. XP-002428499.
European Search Report in 10009799.7 dated Nov. 11, 2010, with English translation of relevant parts.
Tao Dai et al., Blood Characterization from Pulsatile Bioimpedance Spectroscopy, CCECE 2006 (Canadian Conference on Electrical and Computer Engineering), pp. 983-986, Ottawa, Ontario.

* cited by examiner

DIAGNOSTIC MEASURING DEVICE

CROSS REFERENCE TO RELATED APPLICATIONS

This application is the National Stage of PCT/EP2010/001374 filed on Mar. 5, 2010, which claims priority under 35 U.S.C. § 119 of German Application No. 10 2009 011 381.9 filed on Mar. 5, 2009, the disclosure of which is incorporated by reference. The international application under PCT article 21(2) was not published in English.

The invention relates to a diagnostic measuring device for non-invasive determination of at least one physiological parameter of body tissue. The diagnostic measuring device has an optical measuring unit that comprises at least one radiation source for irradiating the body tissue to be examined, and at least one radiation sensor for detecting the radiation scattered and/or transmitted by the body tissue.

It is known that supplying the body tissue with oxygen is one of the most important vital functions of human beings. For this reason, oximetric diagnosis modalities are of great importance in medicine nowadays. So-called pulse oximeters are routinely used. The diagnostic sensor unit of such pulse oximeters typically comprises an optical measuring unit with two light sources, which radiate red or infrared light of different wavelengths into the body tissue. The light is scattered in the body tissue and partly absorbed. The scattered light is finally detected by means of a light sensor in the form of a suitable photocell (photodiode). The intensity of the scattered light detected by means of the light sensor varies as a function of how strongly the body tissue being examined is perfused by oxygen-rich or oxygen-poor blood. Accordingly, the oxygen saturation of the blood can be measured by means of the pulse oximeters. The known pulse oximeters are furthermore able to produce a plethysmographic signal, i.e. a volume pulse signal, which reproduces the variable amount of blood in the microvascular system being detected by the pulse oximeters, which amount changes during a heartbeat (so-called photoplethysmography).

The present invention is based on the task of making available a diagnostic measuring device for non-invasive determination of physiological parameters, which device has a compact structure and can be produced in cost-advantageous manner.

This task is accomplished by the invention, proceeding from a measuring device of the type indicated initially, in that the at least one radiation source is disposed in a hollow reflector, which preferably reflects in diffuse manner.

The embodiment of the measuring device according to the invention permits a particularly compact and robust structure. The hollow reflector can be configured in the manner of a so-called Ulbricht sphere, for example, whereby the geometry of the hollow reflector in the sense of the invention is not restricted to a spherical shape. An Ulbricht sphere is a hollow body coated on the inside so as to be diffusely reflective. The radiation of the light source that is reflected and scattered on the inside is almost ideally diffuse, i.e. the directional characteristics of the radiation source, for example the light-emitting diode, are cancelled out, to a great extent. In this connection, the hollow reflector does not necessarily have to be hollow, but can also be produced from transparent material that is coated on the outside. In this connection, the actual radiation source (for example the LED chip) can be embedded in the material of the hollow reflector, whereby the power supply can be provided by way of a wire connection that is passed out of the hollow reflector. In this manner, the optical measuring unit can be miniaturized. The hollow reflector can be pre-manufactured at low costs, in large numbers, as a very compact component.

According to an alternative embodiment, the hollow reflector can be formed by a chip housing that accommodates the radiation source and/or the radiation sensor within itself, whereby the radiation source and the radiation sensor, in each instance, comprise at least one semiconductor body that is contacted by way of conductor tracks (for example of a so-called lead frame) that run in the interior of the chip housing and/or by way of bond wire connections. In this connection, the chip housing has passage openings on its top, for allowing the radiation emitted by the radiation source to pass through into the body tissue to be examined and/or for allowing the radiation scattered and/or transmitted by the body tissue to pass through. The chip housing essentially forms the mantling of the semiconductor body (of the chips) of the radiation source (LED) and/or of the radiation sensor (photodiode). Furthermore, the connection parts (leads, pins, or balls) are disposed on the chip housing. Thus, the chip housing serves to attach the semiconductor bodies on a circuit board of the measuring device, for example, and to connect the semiconductor bodies with a circuit on the circuit board. The chip housing brings about protection of the semiconductor bodies. The connections of the semiconductor bodies are bonded (connected) to an intermediate material, for example by means of bonding wire. This intermediate material can be a punched metal sheet (lead frame) or a small circuit board as a substrate. The connection to the circuit board of the measuring device takes place exclusively by way of the external connection points of the chip housing. After attachment and wiring of the semiconductor bodies on the intermediate material, it is practical if they are hermetically protected from ambient influences by means of different materials (plastic, ceramic, metal). In this connection, the passage openings for the light entry and/or light exit are disposed on the top of the chip housing. These openings can be closed off by means of transparent plastic (for example epoxy resin), or quartz glass, so that the semiconductor bodies are not directly exposed to the surroundings. According to the invention, the chip housing simultaneously functions as a hollow reflector. For this purpose, the chip housing can be coated with a diffusely reflective material on its inner walls. The radiation of the light source, which is reflected and scattered in the interior, possibly multiple times, is almost ideally diffuse, similar to the case of use of the Ulbricht sphere described above, i.e. the directional characteristics of the radiation source, for example the light-emitting diode, are cancelled out, to a great extent. The radiation of the radiation source therefore leaves the chip housing at a very great angle of radiation of more than 90°, preferably of more than 100°, something that would not be possible with a conventional optic connected with the (miniaturized) chip housing.

According to a preferred embodiment of the measuring device, an EKG unit for detecting an EKG signal by way of two or more EKG electrodes is provided, whereby at least one EKG electrode is assigned to the EKG unit at the housing surface of the sensor housing. Furthermore, a bioelectrical impedance measuring unit is provided, whereby at least one feed or measuring electrode is affixed to the housing surface of the sensor housing, in such a manner that the EKG electrode and the feed or measuring electrode touch the skin surface in the region of the body tissue being detected by the optical measuring unit.

By means of the integration of an optical measuring unit and an EKG unit, according to the invention, a compact arrangement is created, which yields a large number of diagnostic measurement values. These can be evaluated individually or in combination, in order to obtain meaningful information concerning the state of health of the patient being examined, in fast and reliable manner. The compact measuring device can be pre-manufactured as a completely functional part, in cost-advantageous manner, in large numbers, and integrated into diagnosis devices of the most varied kinds. The actual measurement can be carried out in particularly simple and convenient manner. For this purpose, the surface of the sensor housing is brought into contact with the skin, in the region of the body tissue to be examined, something that can take place, for example, by laying a finger of the patient onto the housing surface of the sensor unit. The optical measurement, the EKG recording, and the impedance measurement then take place simultaneously, by way of the skin location that is touching the sensor unit.

The EKG unit of the sensor unit according to the invention serves for determining an EKG signal by way of two or more EKG electrodes. In this way, the functional scope of the sensor unit according to the invention is advantageously expanded as compared with conventional systems. The sensor unit according to the invention makes it possible to detect and evaluate pulse oximetry signals and EKG signals in combination. It is practical, for this purpose, if an evaluation unit for evaluating the time progression of the optically measured volume pulse signals and of the EKG signals is provided. This evaluation unit can be an integral component of the measuring device. Likewise, it can be provided that the evaluation unit is separate from the measuring device, whereby the measurement signals are transmitted to the evaluation unit by way of a suitable data connection. The evaluation unit is able, by means of suitable program control, to automatically recognize the R spikes in the EKG signal, for example. In this way, the precise time point of the heartbeat is determined automatically. Furthermore, the evaluation unit is able, on the basis of suitable program control, to recognize the maxima in the volume pulse signal. The time point of arrival of a pulse wave triggered during a heartbeat at the peripheral measurement location detected by the sensor unit can be determined on the basis of the maxima in the volume pulse signal. Thus, finally, the time interval between an R spike in the EKG signal and the subsequent maximum in the volume pulse signal can be determined. This time interval is a measure of the so-called pulse wave velocity. On the basis of the pulse wave velocity, a statement concerning the blood pressure can be made, on the one hand. This is because shortening of the pulse wave velocity is accompanied by an elevation in blood pressure, while lengthening of the pulse wave velocity permits the conclusion of lowering of blood pressure. However, precise determination of the blood pressure from the pulse wave velocity is not possible; only tendencies can be indicated. Furthermore, the pulse wave velocity is dependent on the density of the blood and, in particular, on the elasticity of the blood vessel walls (for example of the aorta). In turn, a conclusion concerning arteriosclerosis that might be present can be drawn from the elasticity of the blood vessels. The absolute values of the heart rate, heart rate variability, and corresponding cardiac arrhythmias can also be included in this evaluation. For example, arrhythmias such as sinus tachycardia, sinus bradycardia, sinus arrest, and so-called escape beats can be determined automatically. Furthermore, statements concerning the time duration of the atrial contraction as well as the duration of relaxation of the heart chamber, etc., can be established on the basis of the EKG signal. Furthermore, preliminary diagnoses with regard to so-called blocks in the line of the electrical excitation signals at the heart (AV block, bundle branch block, etc.) and also with regard to perfusion problems or infarctions, are also possible. Other irregularities in the pulse progression can be determined on the basis of the volume pulse signal.

The invention is based, among other things, on the recognition that the possibility of determining metabolic parameters is opened up by means of combining different diagnosis modalities in a single measuring device.

According to the invention, a conventional (optical) oximetry unit is therefore combined not just with an EKG unit, but also with a bioelectrical impedance measuring unit, in a single measuring device. The composition of the body tissue being examined, for example, can be determined from the measurement signals obtained by means of the bioelectrical impedance measuring unit. On this basis, it is then possible, preferably by means of a suitable program-controlled evaluation unit, which is connected with the measuring units of the measuring device according to the invention, to determine the capillary oxygen saturation in the tissue from the oximetric signals of the sensor unit. The arterial oxygen saturation ($SaO_2$) and the venous oxygen saturation ($SvO_2$) determine the capillary (arteriovenous) oxygen saturation ($StO_2$), depending on the type of tissue being examined. The following holds true:

$$K^*SvO_2 + (1-K)^*SaO_2 = StO_2,$$

where K is a tissue-dependent correction factor that depends on the volume ratio of arteries to veins in the tissue being examined. On average, this value lies slightly below 0.5. The value decisive for the tissue in question can be determined, according to the invention, by measuring the bioelectrical impedance, in order to then determine the venous oxygen saturation from the above formula. The sensor unit according to the invention can be used to determine the perfusion V, i.e. the perfusion-related volume variation of the body tissue being examined. Finally, according to the equation $$VO_2 = V^*(SaO_2 - SvO_2)$$

the local oxygen consumption $VO_2$ can then be calculated; this represents a measure of the metabolic activity at the measurement location.

Feed or measuring electrodes are disposed on the housing surface of the sensor housing for the bioelectrical impedance measurement, so that the bioimpedance measurement can take place simultaneously with the oximetry measurement and EKG measurement. In this connection, the same region of the body tissue, namely the location where the patient is touching the surface of the sensor housing, is detected simultaneously by all the measurement modalities.

According to the invention, at least one EKG electrode and at least one feed or measuring electrode of the impedance measuring unit are disposed on the surface of the sensor housing. It is practical if the other EKG electrode and, if applicable, another feed and measuring electrode of the impedance measuring unit, are disposed in such a manner that the patient can touch all the electrodes with different extremities, for example one of the electrodes, in each instance, with each hand.

According to an advantageous embodiment, the measuring device comprises an integrated temperature or heat sensor. This sensor can be used to determine the local heat production. In the simplest case, the temperature sensor (for example an NTC element) is configured for measuring the surface temperature of the skin at the measurement location.

Preferably, a location-resolved, time-resolved, and depth-resolved heat measurement at the measurement location is possible by means of the heat sensor. Based on the heat exchange, conclusions can be drawn with regard to the local metabolic activity. Furthermore, the heat sensor is suitable for determining the local perfusion. With regard to more detailed background information concerning heat measurement, reference is made to the publication by Nitzan et al. (Meir Nitzan, Boris Khanokh, "Infrared Radiometry of Thermally Insulated Skin for the Assessment of Skin Blood Flow," Optical Engineering 33, 1994, No. 9, p. 2953 to 2956). In total, the heat sensor yields data that can advantageously be used to determine metabolic parameters.

A combination of the aforementioned measurement methods, according to the invention, namely oximetry, EKG measurement, temperature measurement or heat measurement, and bioelectrical impedance measurement, is particularly advantageous. All the measurement signals can be evaluated and combined by means of a suitable algorithm. A high level of efficacy, redundancy, and reliability in the recognition of pathological changes is achieved by means of combining the different measurement modalities. All the parameters can advantageously be combined into a global index that can easily be interpreted by the user and gives him/her a direct and well-founded indication of his/her general state of health.

The combination of the different measurement modalities, which are brought together in the measuring device according to the invention, as described above, is furthermore advantageous because in this way, a non-invasive indirect measurement of the glucose concentration is possible. The determination of the blood glucose level by means of the device according to the invention will be explained in greater detail in the following:

The metabolism of the human body, in the normal state, i.e. at rest and in the so-called thermoneutral zone, is essentially determined by the glucose metabolism. For this reason, the glucose concentration in the cells of the body tissue, in this normal state, can be described as a pure function of heat production and of oxygen consumption. The following applies:

$$[Glu]=f_1(\Delta T, VO_2)$$

where [Glu] stands for the glucose concentration. The heat production $\Delta T$ can be determined by means of the heat sensor of the sensor unit according to the invention, for example from the difference between the arterial temperature and the temperature that the skin surface would reach in the case of perfect thermal insulation ($\Delta T=T_\infty - T_{artery}$). $f_1(\Delta T, VO_2)$ indicates the functional dependence of the glucose concentration on the heat production and on the oxygen consumption. The oxygen consumption is obtained, as has already been described above, from the difference between venous and arterial oxygen saturation and perfusion. To determine the glucose concentration during or directly after food intake, however, a correction term has to be taken into consideration, which reproduces the proportion of the fat metabolism as part of the energy metabolism. It then holds true that:

$$[Glu]=f_1(\Delta T, VO_2)+X*f_2(\Delta T, VO_2)$$

X is a factor that is negative after food intake. In this connection, X depends on the composition of the food taken in. In particular, X is dependent on the ratio by which fat and carbohydrates are involved in the metabolism. The factor X can be determined, as has been described above, on the basis of the time progression of the pulse wave velocity. X is 0 if pure carbohydrates or glucose directly are consumed. The amount of X increases, the greater the proportion of fat in the food consumed. To determine the correction factor X from the time progression of the pulse wave velocity, the blood pressure amplitude and/or the pulse, a calibration for adaptation to the user of the device, in each instance, will normally be necessary. $f_2(\Delta T, VO_2)$ indicates the functional dependence of the glucose concentration on the heat production and on the oxygen consumption, for the fat metabolism.

The measuring device according to the invention can therefore be used to determine the local glucose concentration from the local oxygen consumption and the local heat production. For this purpose, the measuring device has the suitable measuring modalities. The determination of the oxygen consumption can take place, as has been explained above, by means of combining oximetry with a bioelectrical impedance measurement. In order to determine the heat production, the aforementioned heat sensor is then additionally required. In order to finally be able to determine the glucose concentration according to the functional relationship indicated above, the correction factor X should also be determined, for example from the time progression of the pulse wave velocity. This can take place, as has also been explained above, by means of a combined measurement of EKG signals and plethysmographic signals. It is therefore practical if a pulse oximeter, an EKG unit, a bioelectrical impedance measuring unit, and a heat sensor are combined in the measuring device according to the invention.

The method outlined above at first allows only a determination of the intracellular glucose concentration. The following relationship exists with the blood glucose concentration, in simplified terms:

$$[Glu]_{cell}=a+b*\ln(c*[Glu]_{blood})$$

The constants a, b, and c depend on the individual physiology of the patient being examined. These parameters can be determined by means of corresponding calibration, for example by means of a comparison with blood glucose values determined invasively, in conventional manner.

According to the invention, the optical measuring unit, the EKG unit, the impedance measuring unit, and, if applicable, the temperature or heat sensor, are accommodated in a common sensor housing. It is practical if the at least one EKG electrode and the at least one feed or measuring electrode of the impedance measuring unit are configured as a flat foil or sheet made of electrically conductive material, on the top of the sensor housing. In this connection, the sheet or foil can have at least one recess for passage of the radiation emitted by the at least one radiation source into the body tissue to be examined, or for passage of the radiation scattered and/or transmitted by the body tissue into the radiation sensor. Another recess can be provided for the temperature or heat sensor. The radiation source, the radiation sensor, and the temperature or heat sensor can be disposed on a common circuit board, within the sensor housing. Thus, the required measuring modalities are combined in the sensor housing, which forms a unit that can be easily and flexibly integrated into any desired diagnosis device. The sensor housing can have dimensions of less than 1 cm×1 cm×1 cm, so that it can be easily and flexibly used in the sense of the invention. In this connection, it is practical to use at least one EKG electrode simultaneously also as a feed or measuring electrode for the bioimpedance measurement. In total, an extremely compact integrated measuring device is obtained, which contains different measuring modalities. The same region of the body tissue to be examined (for example a fingertip of a patient that is touching the surface of the sensor housing) can be detected by all the measuring modalities, in order, as has been explained above, to examine the metabolism and the cardiovascular system of the patient at the same time. This makes conducting a measurement extremely simple and effective.

According to a preferred embodiment of the invention, the bioelectrical impedance measuring unit is set up for detecting an impedance measurement signal from the skin surface, by way of at least one pair of measuring electrodes. In this connection, the electrode distance of the pair of measuring electrodes amounts to less than a millimeter to as much as several centimeters, in such a manner that during the measuring process, both electrodes of the pair of measuring electrodes touch the skin surface of the patient being examined in the same region, at the same time, for local detection of the impedance measurement signal. By means of shortening the electrode distance to less than a millimeter to as much as several centimeters, integration does not take place over the entire body, as is the case with conventional bioimpedance measuring methods, but rather the bioelectrical impedance is recorded locally. According to the invention, all the electrodes touch one and the same local region of the skin surface, i.e. all the electrodes are touched with the same body part (for example hand, finger, foot, or toe) of the patient being examined.

It is practical if the measuring device according to the invention has a pair of feed electrodes for applying an alternating current of variable frequency to the body tissue of the patient being examined, by way of the skin surface, for measuring the local resistance and reactance, specifically in the region of the skin surface that touches the measuring electrodes.

Preferably, the distance between the feed electrodes, corresponding to the measuring electrodes, amounts to a few millimeters to several centimeters. An embodiment in which the measuring and feed electrodes are configured as contact strips that run parallel to one another has proven to be particularly advantageous. This makes it possible to determine the local impedance of the body tissue without any distorting influences, for example caused by transition resistances between electrodes and skin surface.

To produce the alternating current of variable frequency, the measuring device according to the invention has an alternating current generator. The impedance measurement signal is digitalized by an analog/digital converter, and afterwards subjected to discrete Fourier transformation (DFT). The DFT algorithm then yields the real and the imaginary part of the impedance, i.e. the resistance value and the reactance value. These values can be processed further digitally, for an evaluation.

Preferably, the electrode distance amounts to as much as maximally 10 cm, particularly preferably 50 micrometers to 5 cm, furthermore preferably 100 micrometers to 1 cm, most preferably 1 mm to 5 mm.

It is possible to determine local time changes in the impedance by means of the configuration of the measuring device according to the invention. For this purpose, it is practical if the measuring device has an evaluation unit connected with the impedance measuring unit. The evaluation unit can be program-controlled, so that the evaluation of the impedance measurement signals can be flexibly implemented, by means of software.

For example, the local bioimpedance changes on the basis of the changing amount of blood over the course of a pulse beat, thereby making it possible to determine the heart rate by way of the local bioelectrical impedance. In this connection, the pulse amplitude is determined at the same time, as an important physiological parameter. It has been shown that this pulse amplitude correlates with the body temperature, i.e. it is possible to determine the temperature of the body location being examined, using the bioimpedance analysis. Furthermore, the local bioimpedance depends on the amount of fluid, i.e. on the local amount of blood in the tissue being examined, thereby making it possible to determine the local perfusion (the local volume variation that is related to perfusion, for example in the form of a volume pulse signal) of the tissue being examined. Finally, the local bioelectrical impedance of the body changes as a function of food intake, so that the metabolism, which is known to be determined by the blood glucose level, can be examined using the bioimpedance. The measuring device according to the invention thus allows non-invasive monitoring of the blood glucose value, also by way of the impedance measuring unit, whereby the effect of glucose and the energy demand of physiological reactions in the body initiated by glucose, respectively, are examined. It is possible to make statements concerning the blood glucose level and its time progression based on the recorded impedance measurement signals, by means of a suitable algorithm that is implemented in the evaluation unit by means of software.

According to another preferred embodiment of the measuring device according to the invention, a fixation device is provided for fixing a body part, for example a finger of the patient being examined, in place. In the case of impedance measurements and also in the case of pulse oximetry measurements, the contact pressure of the body tissue (for example the finger) on the optical sensor or on the measuring and feed electrodes of the impedance measuring device, respectively, has a significant influence on the measurement signals. According, it can be practical to ensure a defined contact pressure by means of the fixation device. The fixation device can comprise an inflatable air cushion, for example, which (gently) presses the corresponding body part against the measuring and/or feed electrodes or against the optical sensors, and fixes it in place there. It is advantageous that movements of the body part that could distort the measurement result are also prevented by the fixation. The fixation device can also be a finger clamp of a usual kind.

In another advantageous embodiment of the measuring device according to the invention, a plurality of feed and/or measuring electrodes is disposed in the form of a matrix. This makes it possible to produce different spatial configurations in the alternating current feed and in the voltage measurement. The additional data obtained in this connection make it possible to draw conclusions concerning the pH value, the $pCO_2$ value, the $pO_2$ value, as well as the electrolyte metabolism ($Na^+$, $K^+$, $Ca^{2+}$, $Mg^{2++}$ concentration, etc.).

The optical measuring unit of the measuring device according to the invention, as has been explained above, has a radiation source for irradiating the body tissue being examined with electromagnetic radiation, and at least one radiation sensor for detection of the radiation scattered and/or transmitted by the body tissue. Usual light-emitting diodes or also laser diodes, which emit optical radiation, i.e. light in the corresponding spectral range, are possible as a radiation source. It has proven to be particularly advantageous if the radiation absorption in the body tissue being examined is measured at at least two or better three different light wave lengths, using the device according to the invention, in order to determine the oxygen concentration of the blood and the perfusion of the tissue from this.

According to a practical embodiment, the optical measuring unit of the measuring device according to the invention has at least two radiation sensors for detection of the radiation scattered and/or transmitted by the body tissue, whereby the radiation sensors are disposed at different distances from the radiation source. This opens up the possibility of drawing conclusions concerning the distance traveled by the radiation in the body tissue, in each instance. On this basis, the oxygen concentration in the blood and in the tissue can be examined in tissue layers at different depths. In this connection, advantage can be taken of the fact that the measurement signals from the tissue layers that lie deeper are more strongly influenced by the arterial blood, while in the regions closer to the surface, the radiation absorption is influenced more strongly by the blood in the capillary vascular system. It is also. practical to use one radiation sensor for detection of transmitted radiation and another radiation sensor for detection of radiation scattered (back) on body tissue. The measurement signals detected in transmission, are more strongly influenced by the absorption in the arterial blood, while the scattered radiation is mainly derived from tissue close to the surface, and therefore permits conclusions concerning the absorption and therefore the oxygen content in the capillary vascular system.

An embodiment of the measuring device according to the invention in which the emission of the light of the at least one radiation source takes place in such a manner that different volume regions of the body tissue being examined are selectively irradiated is advantageous. For this purpose, two radiation sources can be provided, for example, which irradiate the different volume regions of the body tissue being examined. In this way, a differential measurement of the light absorption can be implemented in simple manner. This makes it possible to examine metabolism-induced changes in the perfusion of the body tissue being examined, with oxygen-rich or oxygen-poor blood.

In this connection, advantage is taken of the fact that the local oxygen consumption changes as a function of the metabolic activity of the tissue. The determination of the variable oxygen consumption in turn permits conclusions concerning the local energy consumption, which correlates directly with the oxygen consumption. It is particularly interesting that in turn, this permits conclusions concerning the glucose level. Thus, the measuring device according to the invention advantageously also allows non-invasive determination of the blood glucose level. These volume regions, which are selectively irradiated, in each instance, should be affected differently with regard to perfusion with oxygen-poor or oxygen-rich blood. This can be achieved, for example, in that the at least two radiation sources have different spatial emission characteristics. Thus, a light-emitting diode and a laser that have similar wavelengths (for example 630 nm and 650 nm) can be used as radiation sources, for example. However, the two radiation sources differ in terms of the beam width of the emission. While the light-emitting diode, for example, radiates into the body tissue being examined at a great beam width, the light of the laser diode enters into the body tissue at a very small beam width. This has the result that different volume regions of the body tissue are detected by the two radiation sources. Because of the great beam width, a greater volume region of the non-perfused epidermis is detected by the light-emitting diode than by the laser. The non-perfused epidermis is practically not affected by a change in the hemoglobin concentration. Accordingly, the intensity of the radiation of the light-emitting diode that is scattered and/or transmitted by the body tissue is less greatly dependent on a change in the hemoglobin concentration than the intensity of the radiation of the laser. A prerequisite is that the wavelength of the radiation emitted by the two radiation sources, in each instance, is selected to be such that the radiation is absorbed to a different degree by oxyhemoglobin and deoxyhemoglobin, respectively. The wavelength should therefore lie between 600 and 700 nm, preferably between 630 and 650 nm.

The measuring device according to the invention can advantageously be configured for determining a metabolic parameter from the radiation of the at least one radiation source that is scattered and/or transmitted by the body tissue. If oxygen is consumed in the body tissue being examined, oxyhemoglobin is converted to deoxyhemoglobin. The change in the concentration ratio of oxyhemoglobin and deoxyhemoglobin can be determined by means of a comparison of the radiation derived from the selectively irradiated different volume regions of the body tissue. This in turn results in the local oxygen consumption and from it, in the final analysis (indirectly), the blood glucose level.

An optic that brings about directed emission into the body tissue can be linked with the hollow reflector provided according to the invention. Furthermore, the hollow reflector can have an exit opening through which diffuse emission into the body tissue takes place. In this manner, the optical measurement described above can take place at different volume regions of the body tissue.

If the hollow reflector is a chip housing, as has been described above, the optic can advantageously be formed by a transparent plastic material (for example silicone resin or epoxy resin) that fills the chip housing. This allows a very compact and robust structure.

For practical use, the measuring device according to the invention can be connected with any desired program-controlled device, for example a computer, a mobile telephone, a handheld, etc., whereby the functions for evaluation of the measurement signals detected are implemented by software that runs on the program-controlled device. Because of the small size of the sensor housing, the sensor housing can also be integrated into any desired accessory, such as, for example, a pair of glasses, a wristwatch, a piece of jewelry, or the like, or into an article of clothing (so-called "smart clothes"). In this embodiment, for example, the data processing electronics that are present in the program-controlled device in any case are used for processing the measurement signals obtained. This processing can easily be done by making available corresponding software. At the same time, the diagnostic data determined by means of the software can be stored. This storing makes it possible to follow up on and document the course of an illness and the effects of a corresponding therapy. It is practical that remote data transmission of the diagnostic data detected and evaluated by means of the measuring device can also take place. The data transmission can take place, for example, by way of a data network (for example the Internet). Alternatively, the diagnostic data can be transmitted by way of a mobile radio network, if the measuring device according to the invention is integrated into a mobile telephone, for example. The raw measurement signals or the evaluated diagnostic data can be transmitted, for example, to a central location ("healthcare center") for more thorough analysis and documentation, as well as for monitoring of the development of individual values over time. There, the data are evaluated by means of suitable analysis algorithms, for example, taking stored patient data (including data concerning chronic illnesses or prior illnesses) into account, if applicable. The result in turn can be sent back to the mobile telephone, for example, by way of the data or communications network, in each instance, in order to inform the user of the device about his/her state of health, accordingly. If necessary, further targeted measurements by means of the device according to the invention can be initiated from the central location. Furthermore, for the purpose of an expanded anamnesis, inquiries can be transmitted to the patient by way of the data or communications network, based on the evaluation results. The data and evaluation results can be automatically transmitted to a treating physician. If there are indications of a medical emergency based on the measurement and evaluation results, the required measures (for example automatic alarm to emergency medical services) can be initiated immediately. Another advantage of remote data transmission is that the required software for evaluation of the measurement signals does not have to be implemented in the device itself, but rather merely has to be kept available and administered at the central location where the data are received.

In the case of pulse oximetry measurements, the contact pressure of the body tissue (for example the finger) on the optical sensor has a significant influence on the measurement signals. Accordingly, it can be practical to equip the measuring device according to the invention with means for determining the contact pressure of the body tissue. In this connection, this can be a conventional pressure sensor, for example in the form of a piezoresistive element. Optical methods for determining the contact pressure are also possible. It is also possible to determine the contact pressure from the (pulse oximetry) signals themselves, since the contact pressure has a characteristic effect on the measurement signals. The contact pressure that is determined can then be taken into consideration in the further evaluation of the measurement signals, in order to compensate the influence of the contact pressure on perfusion, for example.

Exemplary embodiments of the invention will be explained in greater detail in the following, making reference to the drawings. These show.

Figure 1:
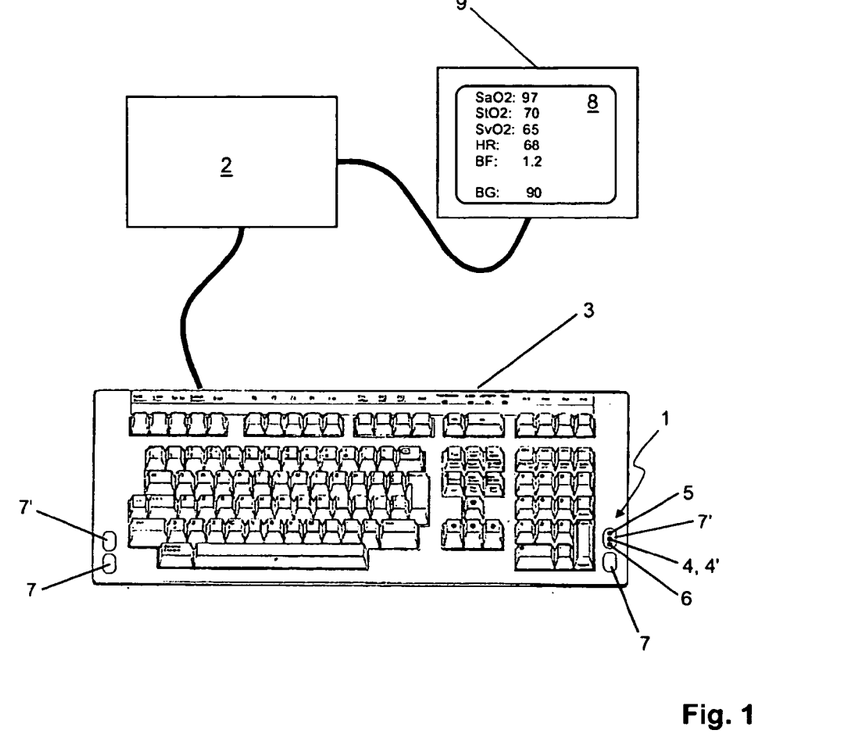
FIG. 1 schematic view of the integration of the measuring device according to the invention into a computer keyboard.

FIG. 1 shows a measuring device according to the invention, indicated as a whole with the reference number 1, which is integrated into a computer system consisting of computer 2 and keyboard 3. The measuring device 1 has different measurement modalities, which are accessible at the user interface of the keyboard 3. The user of the computer system touches this interface with his/her fingertips to perform a measurement. Light sources 4, 4', for example in the form of light-emitting diodes, are integrated into the measuring device 1, which sources are able to emit light at different wavelengths. For this purpose, different light-emitting semiconductor elements are accommodated in a common sensor housing (the housing of the keyboard in FIG. 1). The use of light wave guides for guiding the light from various light sources to the user interface of the keyboard 3 is also possible (see below). Furthermore, the measuring device 1 comprises one or more photosensors 5. The photosensors are disposed in the immediate vicinity of the light source 4 or 4', respectively. The sensors 5 receive the light of the light source 4 or 4' that is scattered in the tissue at the fingertip of the user. Furthermore, a heat sensor 6 is provided directly next to the light source 4 or 4'. In this way, it is guaranteed that the determination of the perfusion using the heat measurement takes place at the same measurement location as the optical measurement. Furthermore, four electrodes 7 or 7', in total, for measuring the bioelectrical impedance are provided. The user of the device touches two electrodes 7 and 7' with one hand, at the same time, in each instance. One of the two contact surfaces serves for applying an electrical current at the measurement location, while the other contact surface is used for measuring voltage. In this manner, it is ensured that the measurement results are not influenced by the contact resistances of the measuring electrodes. The two electrodes designated with the reference number 7 are furthermore used as EKG electrodes of an EKG unit integrated into the measuring device 1. The two electrodes are touched with the fingertips, in each instance, so that a two-point lead (arm-to-arm measurement) is obtained. The measurement signals recorded by means of the measuring device 1 integrated into the keyboard 3 are processed by means of the computer 2. The physiological parameters obtained in this way are then output on a display surface 8 of a monitor 9 connected with the computer 2. For example, the arterial ($SaO_2$), capillary ($StO_2$), and venous ($SvO_2$) oxygen saturation are displayed. Furthermore, the heart rate (HR) and the fat content of the tissue (BF) that are determined are displayed. Finally, a blood glucose value (BG) is also displayed. The user can determine the physiological parameters that interest him/her, at any time. For this purpose, he/she merely places the fingers with which he/she otherwise activates the keys of the keyboard 3 on the electrodes 7, 7'. The parameters are then immediately displayed on the monitor 9, after the signals are processed by means of the computer 2. The user of the device 1 therefore practically does not have to interrupt his/her work on the computer 2 in order to determine the physiological parameters.

In the exemplary embodiment of the measuring device 1 shown in FIG. 1, two radiation sources 4 and 4' are provided, which irradiate different volume regions of the body tissue being examined. For this purpose, the two radiation sources 4 and 4' have different spatial emission characteristics, namely different emission angles. The radiation source 4 is a light-emitting diode, while the radiation source 4' is a laser, for example a so-called VCSEL laser (English: "vertical cavity surface emitting laser"). Both the light-emitting diode 4 and the laser 4' emit light having a very similar wavelength (for example 630 nm and 650 nm), but with different beam widths (for example 25° and 55°). With the arrangement shown in FIG. 1—as has already been explained above—it is possible to perform a differential measurement of metabolism-induced changes in the oxygen content in the blood. For this purpose, the wavelength of the radiation emitted by the two radiation sources 4 and 4', in each instance, must lie in a range in which the light is absorbed to a different degree by oxyhemoglobin and deoxyhemoglobin. For an absolute measurement of the oxygen content of the blood (oxygen saturation), additional radiation sources (not shown in FIG. 1) must be present, the light wavelength of which lies in a spectral range in which the light absorption of oxyhemoglobin and deoxyhemoglobin is essentially the same (so-called isobestic point). The light emitted by the light-emitting diode or by the laser, respectively, can be guided to the corresponding location at the user interface of the keyboard by means of corresponding light guide fibers. In this case, the corresponding fiber ends are shown with the reference numbers 4 and 4' in FIG. 1. It is possible to couple the light-emitting diode and the laser to the corresponding fibers in such a manner that they radiate light into the body tissue to be examined at the desired different beam width. Accordingly, different volumes of the body tissue are examined with the two radiation sources. Because of the greater beam width, the proportion of the non-perfused epidermis is greater in the body tissue examined by means of the light-emitting diode than in the case of the laser. The light that is scattered in the body tissue and partly absorbed, both from the radiation source 4 and from the radiation source 4', is detected by means of the sensors 5. The sensors 5 do not have to be disposed directly on the surface of the measuring device 1. Instead, the light can be passed to the sensors disposed in the interior of the measuring device 1, by way of light guide fibers. In order to differentiate the light of the radiation source 4 from the light of the radiation source 4', the two light sources 4 and 4' can be operated with different time modulation, whereby the signals detected by means of the sensors 5 are demodulated accordingly. Alternatively, it is possible to differentiate the radiation of the two radiation sources 4 and 4' on the basis of the different wavelength. The radiation intensity of the radiation emitted by the radiation sources 4 and 4' is weakened with the path length when passing through the body tissue, whereby the relationship between the intensity weakening and the concentration of the absorbing substance (oxygenated hemoglobin) is given by the known Beer-Lambert law. The parameters of the intensity weakening that are of interest can be determined by means of the sensors 5 shown in FIG. 1, specifically separately for the volume regions of the body tissue being examined, as detected by the radiation sources 4 and 4', in each instance. The parameters of the intensity weakening that are assigned to the different radiation sources 4 and 4' can be put into relation with one another by means of a suitable program-controlled evaluation unit, in order to carry out a differential measurement in this way. In the simplest case, quotients are calculated, in each instance, from the parameters of the intensity weakening of the radiation of the two radiation sources 4 and 4'. Conclusions concerning changes in the metabolism can then be drawn from changes in these quotients. If, for example, the blood glucose level increases after food consumption, correspondingly more glucose gets into the cells of the body tissue (after a certain time delay), and is converted there. In this connection, oxygen is consumed. The cells receive this oxygen by way of the blood. In this connection, oxygenated hemoglobin turns into deoxygenated hemoglobin, because it gives off oxygen. Accordingly, the ratio of deoxygenated hemoglobin to oxygenated hemoglobin increases. Because of the different beam widths of the radiation of the radiation sources 4 and 4', the changes in the hemoglobin concentration have different effects on the intensity weakening, in each instance. Thus, changes in the hemoglobin concentration can be detected from the quotients of the parameters of the intensity weakening. This makes it possible to indirectly draw conclusions concerning the oxygen consumption. Since the oxygen consumption in turn depends on the blood glucose level, the blood glucose level can also be determined by means of the differential measurement of the radiation absorption, as explained. Supplementally, parallel to the optical measurement, a bioimpedance analysis is carried out, for which purpose the electrodes 7 and 7' shown in FIG. 1 are provided. The purpose of the bioimpedance measurement is, above all, to determine the local perfusion. This can be used as an additional parameter in the determination of the oxygen consumption and thus also of the blood glucose level. Different beam widths of the radiation can also be produced using only one radiation source 4, by using corresponding optical elements (for example beam splitters, lenses, etc.).

Furthermore, it is advantageous to carry out the evaluation of the measurement values in pulse-synchronous manner. This is possible because the measuring device according to the invention has a suitable sensor system for detecting the pulse (for example EKG). Thus, for example, the measurement values obtained by means of optical measurement or impedance measurement can be evaluated, in targeted manner, at the time point of the maximum and/or the minimum of the pulse wave, in order to balance out pulse-related variations. Also, valuable diagnostic data can be obtained from the ratio of the pulse-dependent to the pulse-independent amount of blood in the body tissue being examined, as well as from the pulse-dependent and pulse-independent metabolic data that can be separately detected with the device according to the invention.

Figure 2:
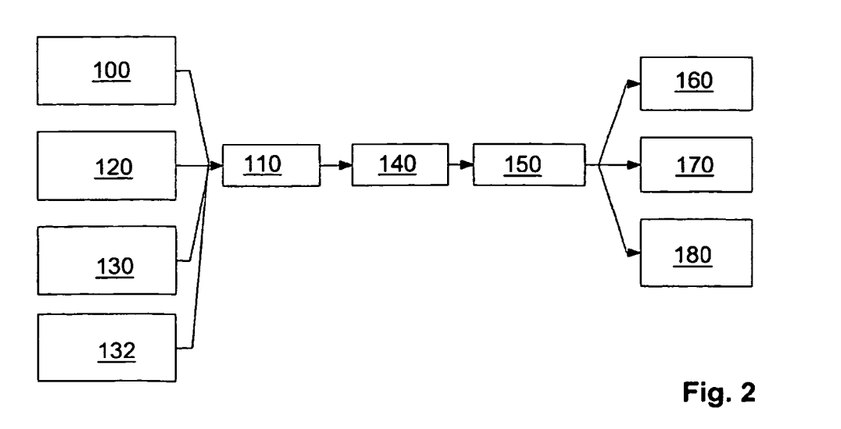
FIG. 2 representation of the function of the measuring device according to the invention, using a block diagram.

FIG. 2 schematically shows the structure of the measuring device 1 according to the invention as a block diagram. The measuring device 1 comprises an optical measuring unit 100 for optically measuring the oxygen concentration in the vascular system of the body tissue at the measurement location, in each instance. The oximetric and plethysmographic signals detected by means of the optical measuring unit 100 are passed to an analysis unit 110. Another essential component of the device 1 is a heat measuring unit 120 for determining the local heat production. The heat measuring unit 120 is a special heat sensor that insulates the body location being examined, in each instance. This location can therefore only take on or give off heat by way of the blood stream. For this reason, it is possible to determine the perfusion and the heat production by means of a time-resolved measurement of the temperature. In the case of strong perfusion, the body location being examined reaches its maximal temperature within a very short period of time. In the case of low perfusion, this takes longer. In addition, a conclusion concerning the arterial temperature can be drawn by way of extrapolation of the measured temperature, since the temperature at the location of the measurement is determined only by the arterial temperature and by the local heat production. The measurement signals detected by means of the heat measuring unit 120 are also passed to the analysis unit 110 for further processing. Furthermore, the device comprises an impedance measuring unit 130 that serves for determining local tissue parameters by means of measuring bioelectrical impedance. The measurement signals of the impedance measuring unit 130 are also processed by means of the analysis unit 110. Finally, according to the invention, an EKG unit 132 is also provided for detecting an EKG signal. The EKG unit 132 is also connected with the analysis unit 110, for processing of the EKG signals. The optical measuring unit 100 has the light source 4 as well as the light sensors 5 of the measuring device 1 shown in FIG. 1 assigned to it. The heat measuring unit 120 is connected with the heat sensor 6. The impedance measuring unit 130 detects measurement signals by way of the electrodes 7 and 7', respectively, of the device 1. The analysis unit 110 performs pre-processing of all the measurement signals. For this purpose, the signal passes through a band-pass filter, in order to filter out interference in the range of the network frequency of 50 or 60 Hz, respectively. Furthermore, the signals are subjected to noise suppression. After passing through the analysis unit 110, the processed signals of the optical measuring unit 100, the heat measuring unit 120, the impedance measuring unit 130, and the EKG unit 132 get into the evaluation unit 140. The evaluation unit 140 is responsible for calculating parameters essential for the diagnosis from the measurement signals. First, the composition of the body tissue being examined (water content, fat content, etc.) is calculated from the measurement signals of the impedance measuring unit 130, which are recorded as a function of time. The arterial oxygen saturation and—based on the tissue parameters determined on the basis of the impedance measurement—the capillary oxygen saturation are calculated from the signals of the optical measuring unit 100. Furthermore, the perfusion and the arterial temperature are determined from the measurement signals of the heat measuring unit 120 and from the plethysmographic data that can be derived from the time-dependent impedance measurements. The pulse wave velocity is determined from the signals of the EKG unit 132 and those of the optical measuring unit 100. Finally, the venous oxygen saturation is calculated from the results of all the calculations that were carried out previously, by means of the evaluation unit 140, and from this, other metabolic parameters, particularly the local oxygen consumption and the glucose concentration at the measurement location, are calculated. The calculation results are interpreted by means of the diagnosis unit 150. The diagnosis unit 150, which is also implemented on the computer 2 as software, serves for evaluating the local metabolic parameters calculated by means of the evaluation unit 140. The evaluation unit 140 and the diagnosis unit 150 are connected with a graphics unit 160, to display the measurement results, and this unit in turn controls the monitor 9. The data obtained can be stored in a memory unit 170, specifically with simultaneous storage of the date and time of the measurement, in each instance. Furthermore, an interface unit 180 is provided, which serves to connect the computer 2 with a data network for transmitting the calculated physiological parameters. All the data and parameters, particularly also the data and parameters stored in the memory unit 170, can be transmitted to a PC of a treating physician, not shown in any detail, by way of the interface unit 180. There, the data can be analyzed in greater detail. In particular, data and parameters recorded with the measuring device 1 over an extended period of time can be investigated for changes, in order to able to draw conclusions from this with regard to the development of an existing illness.

Figure 3:
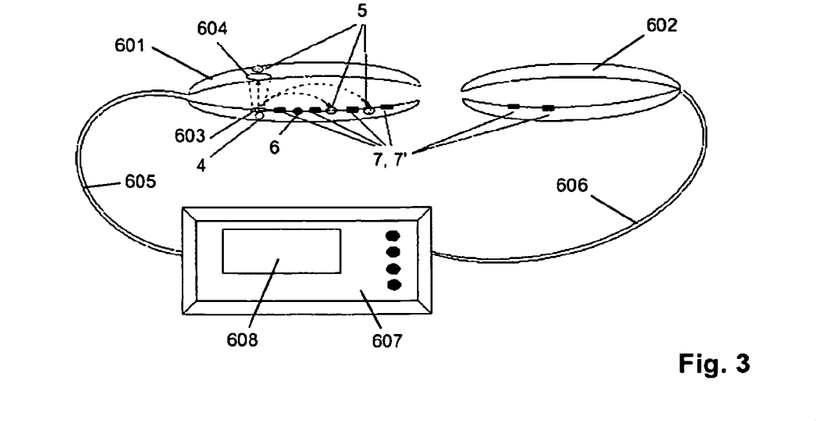
FIG. 3 another exemplary embodiment of the measuring device according to the invention.

FIG. 3 shows an alternative exemplary embodiment of the measuring device according to the invention. This comprises two finger clamps 601 and 602, by means of which a finger of the left and right hand, respectively, is fixed in place on the sensors of the measuring device. The radiation source 4, the radiation sensors 5, the electrodes 7, 7' used for measuring EKG and impedance, as well as the heat sensor 6 are integrated into the finger clamp 601. In this connection, it is a special feature of the exemplary embodiment shown in FIG. 3 that the light produced by the radiation source 4 is measured in two ways by the radiation sensors 5, namely for one thing, in the transmission direction, by means of the radiation sensor 5 that is disposed in the upper part of the finger clamp 601, opposite the radiation source 4, and for another thing, by means of the radiation sensors 5 integrated into the lower part of the finger clamp 601, which detect the light scattered back in the tissue of the finger. Lenses 603, 604 are provided for the transmission measurement from the radiation source 4 and the opposite radiation sensor 5, in each instance. The lens 603 ensures directed emission of the light into the tissue. The lens 604 collects the transmitted light and focuses it on the radiation sensor 5. Only two electrodes 7, 7' are disposed in the finger clamp 602, as counter-electrodes to the electrodes integrated into the finger clamp 601. These serve for measuring EKG (two-point lead) as well as for a (global) bioimpedance measurement. The finger clamps 601 and 602 are connected with a central unit 607 by way of cables 605, 606. The central unit 607 contains the analysis, evaluation, and diagnosis units of the measuring device. Representation of the measurement values obtained takes place by way of the display 608. Different optical measurement values, for example in the form of light intensities detected by way of the radiation sensors, can be measured with the arrangement shown. These are the transmitted intensity $I_T$ and the intensities $I_{RS1}$ and $I_{RS2}$ that are scattered back from different tissue regions. A measurement using an (artificial) standard material can be carried out for calibration. This then yields the value $I_{ref}$. These four measurement values form the basis for the further evaluation.

Figure 4:
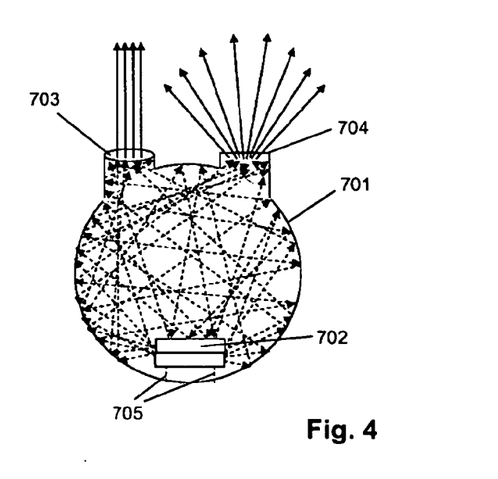
FIG. 4 hollow reflector with radiation source.

FIG. 4 shows a hollow reflector 701, in which one (or several) LED(s) 702 is/are disposed as a radiation source. This is an SMD LED, which emits light in all spatial directions. Other types of light sources are also possible, according to the invention. The light of the LED 702 is diffusely reflected at the inner surfaces of the hollow reflector 701. The hollow reflector 701 is configured in the manner of an Ulbricht sphere in the case of the exemplary embodiment. An optic 703 in the form of a collecting lens is linked with the hollow reflector 701. The collecting lens, as indicated in FIG. 4, brings about a directed emission of the light emitted by the LED 702.

Furthermore, the hollow reflector 701 has an exit opening 704, through which diffuse emission into the body tissue takes place. A suitable optic can also be provided in the region of the exit opening 704, in order to achieve the desired emission angle. Different emission angles can be produced, for example, by means of lenses having different focal widths or other optical elements, such as collimators, for example. The arrangement shown in FIG. 4 can advantageously be produced at low cost, in great numbers, as a compact, pre-manufactured unit. The electrical connections 705 of the LED are passed out of the hollow reflector. The hollow reflector can be configured, for example, as a solid body made of transparent plastic, in which the LED 702 is embedded. This body can then be coated with diffusely reflective material (for example aluminum oxide or barium sulfate) on its outside. The deciding factor is that the directional characteristics of the LED are cancelled out by means of diffuse reflection, and then the desired emission characteristics can be predetermined, in accordance with the requirements, in each instance, by uncoupling the light out of the reflector in suitable manner. It is easily possible to accommodate multiple LEDs in a hollow reflector, in order to produce radiation at different wavelengths and uniformly radiate it into the body tissue by way of the optic 703 linked with the hollow reflector 701 or by way of the exit opening 704, respectively.

Figure 5:
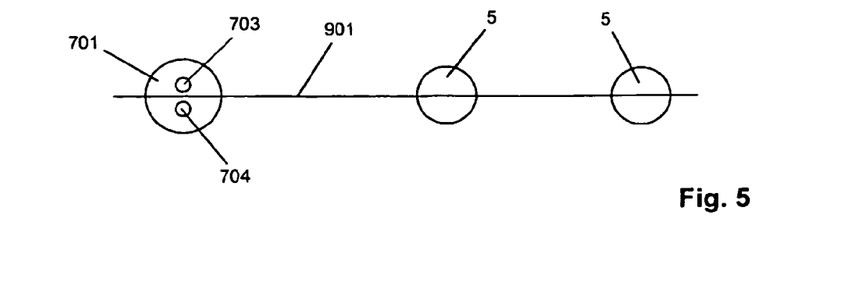
FIG. 5 exemplary embodiment of a configuration of the optical measuring unit of the measuring device according to the invention.

FIG. 5 shows a top view of the sensor system of the optical measuring unit on the surface of the sensor housing of the measuring device according to the invention, which lies against the body tissue to be examined. The top of the hollow reflector 701 can be seen, whereby the optic 703 and the exit opening 704 lie in the plane of the measuring surface. In this connection, the optic 703 and the exit opening 704 are disposed to the left and the right of an axis 901, in each instance. Furthermore, radiation sensors 5 are disposed on the axis 901. Each of the radiation sensors 5 has the same distance, in each instance, from the optic 703 and the exit opening 704. At the same time, the two radiation sensors 5 have different distances from the radiation source. This arrangement opens up the possibility of taking the distance traveled in the body tissue by the detected radiation into consideration, so that the oxygen concentration in the blood and in the tissue can be examined in tissue layers at different depths.

Figure 6:
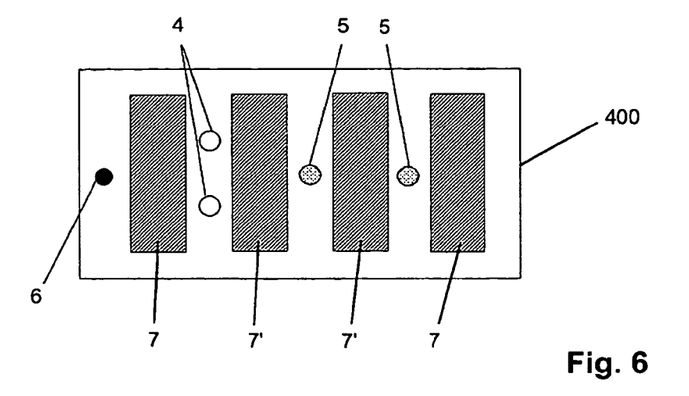
FIG. 6 housing surface of the sensor housing with electrodes, radiation source, radiation sensors, and heat sensor, in a first possible configuration.
Figure 7:
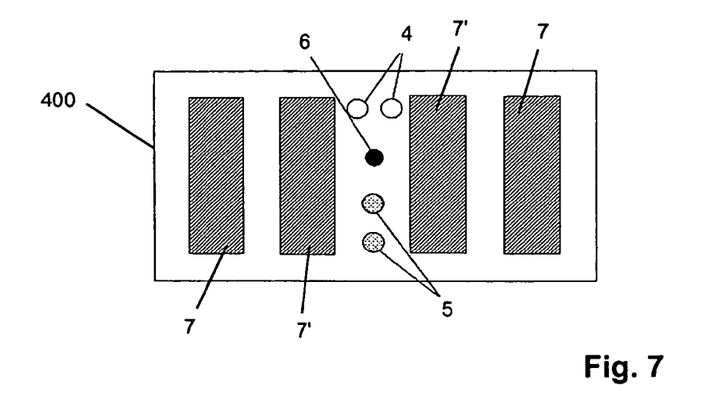
FIG. 7 housing surface of the sensor housing in a second possible configuration.
Figure 8:
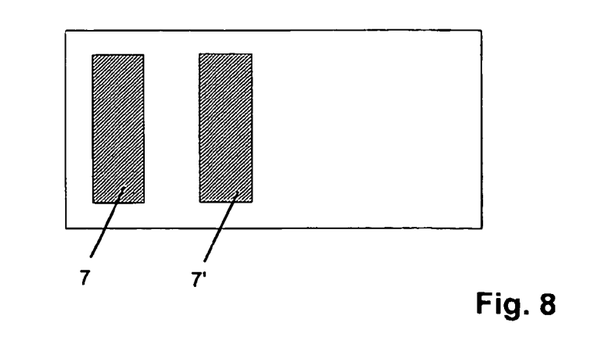
FIG. 8 configuration of the counter-electrodes for measuring EKG and bioimpedance.

FIGS. 6, 7, and 8 show different configurations of the sensor system of the diagnostic measuring device according to the invention. FIGS. 6 and 7 show two different top views of the surface of the sensor housing. The electrodes 7, 7' are assigned to the EKG unit and to the impedance measuring unit of the measuring device. FIG. 8 shows the placement of counter-electrodes that are used for an arm-to-arm measurement of the EKG and for measuring bioelectrical impedance. The impedance measuring unit comprises the electrodes 7 shown in FIGS. 6 and 7, for feeding in electrical alternating current, and measuring electrodes 7' for measuring the impedance of the body tissue, for example in the region of the finger of the patient being examined (see FIG. 3). Because of the four-point measurement, transition resistances between the electrodes 7, 7' and the body tissue do not distort the measurements. The distance between the electrodes 7, 7' can amount to only a few millimeters to a few centimeters. During the measuring process, all four electrodes that are shown in FIGS. 6 and 7 simultaneously touch the same region of the skin surface, for example on the finger of the patient. It is possible to measure complex impedance by means of feeding in alternating current of variable frequency. The measurement signal is detected by means of a voltage meter (not shown), by way of the electrodes 7'. The measurement signal is digitalized by means of an analog/digital converter (also not shown), and afterwards subjected to discrete Fourier transformation. The result then yields the real part and the imaginary part of the impedance, i.e. the resistance value and the reactance value. In the exemplary embodiments shown in FIGS. 6 and 7, the electrodes 7, 7' are configured as strips that are spaced parallel apart from one another, and are electrically insulated from one another by means of the interstices that lie between them. The light sources 4, the radiation sensors 5, as well as the heat sensor 6 are disposed in the interstices. All the sensors are in contact with the body tissue to be examined.

Figure 9:
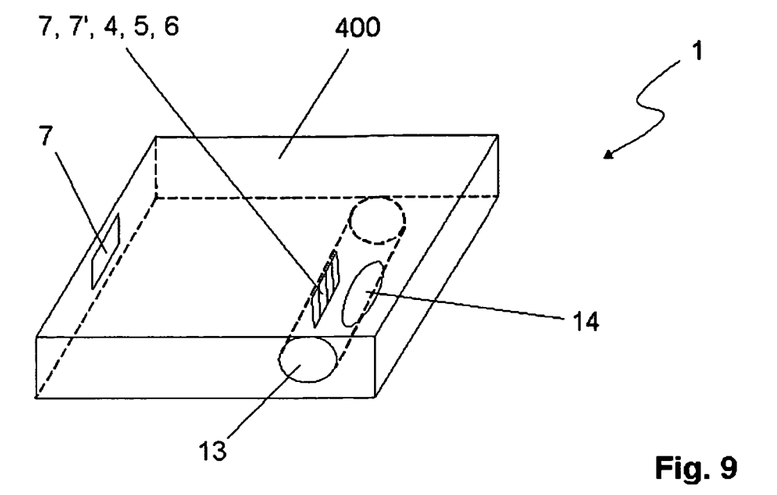
FIG. 9 another exemplary embodiment of the measuring device according to the invention.

FIG. 9 schematically shows another exemplary embodiment of the measuring device 1 according to the invention. An EKG electrode 7 is affixed on the outside of the housing 400. This electrode is touched with the finger of one hand. The finger of the other hand is introduced into a tubular opening 13. The electrodes 7, 7', a radiation source 4, radiation sensors 5, as well as a heat sensor 6 are situated in the interior of the opening 13. Furthermore, an inflatable air cushion 14 is disposed in the interior of the tube 13, which cushion fixes the finger in place and presses it against the sensors gently and at a defined pressure. Operating keys of the measuring device 1 as well as a display for outputting the measurement results are left out of FIG. 9, for reasons of clarity.

Figure 10:
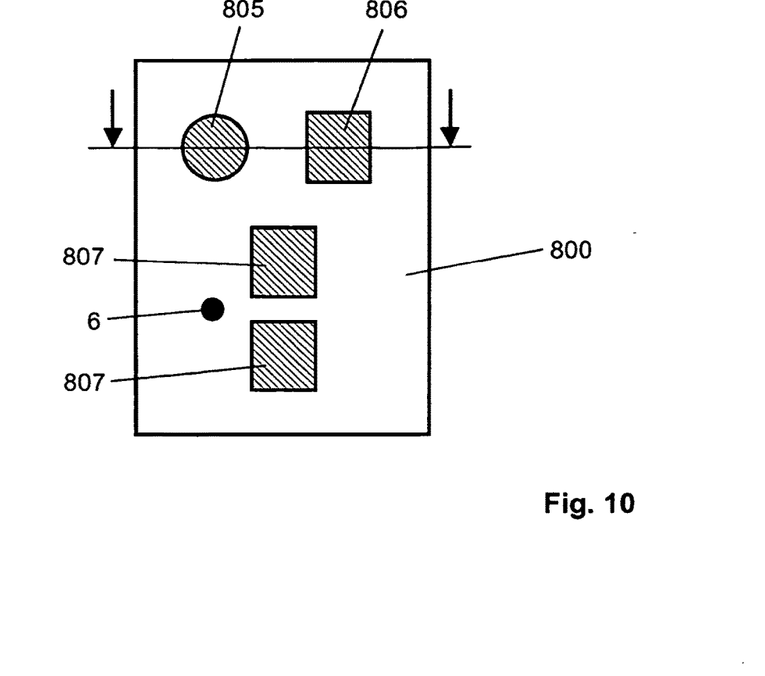
FIG. 10 chip housing as a hollow reflector, in a top view.
Figure 11:
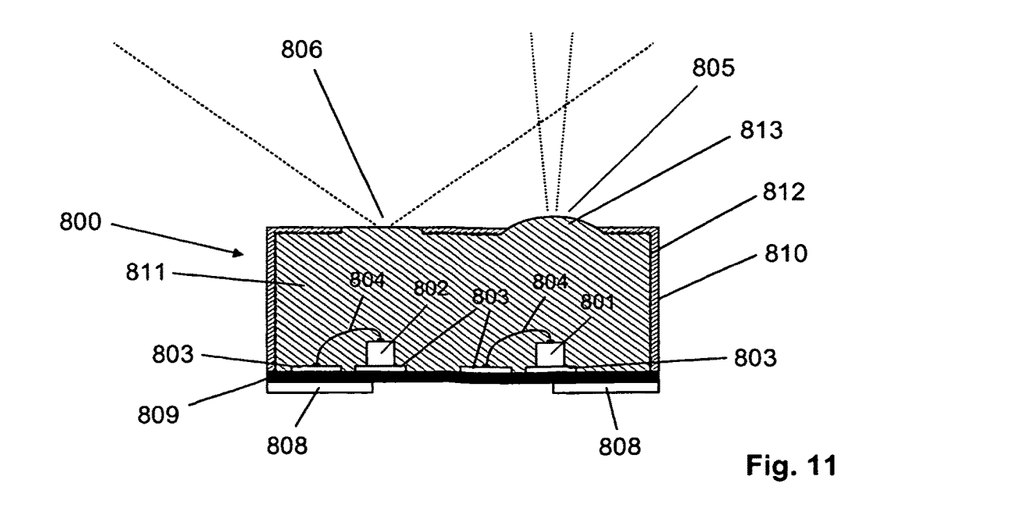
FIG. 11 sectional representation of the chip housing according to FIG. 10.

FIGS. 10 and 11 show a chip housing 800 that forms a hollow reflector in the sense of the invention. The chip housing 800 accommodates the radiation source and the radiation sensor within itself. In the exemplary embodiment shown, two radiation sources having semiconductor bodies 801 and 802 are provided, which are LED chips, for example. Electrical conductor tracks 803 run in the interior of the chip housing. The electrical connections with the semiconductor bodies 801, 802 are produced by means of die-bonding or by way of bond wires 804, respectively. At its top, which can be seen in FIG. 10, the chip housing 800 has passage openings 805, 806, and 807 for exit of the radiation emitted by the semiconductor bodies 801, 802, into the body tissue to be examined, or for entry of the radiation scattered and/or transmitted by the body tissue into the chip housing 800, respectively. Photodiodes (not shown) are disposed behind the passage openings 807, within the chip housing 800, as radiation sensors. The chip housing 800 forms the mantling of the semiconductor bodies 801, 802 and of the photodiodes. Furthermore, electrical connection points 808, by way of which the chip housing 800 can be attached on a circuit board (not shown) of the measuring device according to the invention and connected with a circuit on the circuit board are on the underside of the chip housing 800. The electrical conductor tracks 803 are disposed on a substrate 809 that forms the underside of the chip housing 800. The top is formed by a housing lid 810. The semiconductor bodies 801, 802 attached and wired on the substrate 809 are surrounded by a transparent plastic material 811 (for example epoxy resin, silicone resin, quartz glass, or PMMA), which fills the housing interior, as can be seen in FIG. 11. In the region of the passage openings 805, 806, 807 the housing lid 810 has corresponding recesses. In this manner, semiconductor bodies 801, 802 are not directly exposed to the surroundings. The chip housing functions as a hollow reflector. This means that the radiation emitted by the semiconductor bodies 801, 802 is reflected (multiple times) at the inner surfaces of the chip housing 800. For this purpose, the chip housing 800 can be coated with a diffusely reflective material 812 on its inner walls. Alternatively, the chip housing 800 can be produced from a white, i.e. reflective plastic material. The radiation of the semiconductor bodies 801, 802 reflected and scattered in the interior is almost ideally diffuse. The radiation of the semiconductor body 802, for example, thus leaves the chip housing 800 through the passage opening 806, at a very great emission angle of approximately 110°, into the body tissue to be examined. In the region of the passage opening 805, the transparent plastic material 811 that fills the chip housing 800 forms a collecting lens 813. The collecting lens 813, as indicated in FIG. 11, brings about directed emission of the radiation emitted by the semiconductor body 801, into the body tissue, at an angle of approximately 10°. Furthermore, the heat sensor 6 can be integrated into the chip housing 800.

The invention claimed is:

1. A diagnostic measuring device for non-invasive determination of at least one physiological parameter, the diagnostic measuring device having an optical measuring unit that comprises:
   at least one radiation source for irradiating a body part of a patient,
   at least two radiation sensors configured to detect radiation scattered and/or transmitted by the body part and configured to measure optical measurement values in the form of light intensities comprising transmitted intensity $I_T$ and/or intensities $I_{Rs1}$ and $I_{Rs2}$ that are scattered back from different tissue regions, at least one hollow reflector, the at least one radiation source being disposed in the at least one hollow reflector, and a first radiation exit and a second radiation exit connected to the at least one hollow reflector, and an optic configured to collect and emit radiation, wherein the at least one radiation source emits radiation in the hollow reflector so that a diffusion level of the radiation in the hollow reflector is increased, so that diffused radiation is produced, and so that the diffused radiation is then conducted via the first radiation exit and via the second radiation exit, wherein the first radiation exit comprises or is connected to the optic such that the optic is configured to collect the diffused radiation and to emit the diffused radiation as a first radiation beam at a first opening angle, wherein the second radiation exit is configured to emit the diffused radiation as a second radiation beam differently shaped from the first radiation beam and at a second opening angle, wherein the first radiation beam and the second radiation beam have different spatial characteristics and are configured to irradiate different volume ranges of the body part, and wherein the first opening angle is different from the second opening angle.

2. The diagnostic measuring device according to claim 1, further comprising a temperature or heat sensor.

3. The diagnostic measuring device according to claim 2, wherein the at least one radiation source, and the at least one hollow reflector, the first radiation exit, the second radiation exit, and a first element are disposed in a common sensor housing, and wherein the first element is selected from the group consisting of at least one electrode for EKG measurements, at least one electrode for bioelectrical impedance measurements, and the temperature or heat sensor.

4. The diagnostic measuring device according to claim 1, further comprising at least one electrode configured as a flat foil or sheet.

5. The diagnostic measuring device according to claim 1, further comprising
at least one electrode having at least one recess, and
a temperature or heat sensor,
wherein at least one first element is disposed in said at least one recess, said at least one first element being selected from the group consisting of:
an end of the first radiation exit,
the at least one radiation sensor, and
the temperature or heat sensor.

6. The diagnostic measuring device according to claim 1, further comprising at least one electrode configured to perform an EKG measurement and configured to perform a bioelectrical impedance measurement.

7. The diagnostic measuring device according to claim 1, further comprising a first electrode for bioelectrical impedance measurements and a second electrode for bioelectrical impedance measurements,
wherein a distance between the first electrode and the second electrode is less than 10 cm.

8. The diagnostic measuring device according to claim 1, further comprising at least one feeder electrode for bioelectrical impedance measurements,
wherein the at least one feeder electrode applies alternating current of variable frequency.

9. The diagnostic measuring device according to claim 8, further comprising at least one measuring electrode for bioelectrical impedance measurements,
wherein the at least one feeder electrode and the at least one measuring electrode are configured as contact strips that run parallel to each other.

10. The diagnostic measuring device according to claim 1, further comprising
at least two measuring electrodes for bioelectrical impedance measurements, and
a computer programmed to determine changes of a local impedance measurement signal over time.

11. The diagnostic measuring device according to claim 1, further comprising a sensor housing, measuring and/or feed electrodes, and a fixation device configured to fix the body part of the patient to be examined in place on the sensor housing, the fixation device being selected from the group consisting of:
a finger clamp, and
an inflatable air cushion configured to press the body part against the measuring and/or feed electrodes.

12. The diagnostic measuring device according to claim 1, wherein the at least two radiation sensors are disposed at different distances from the at least one radiation source.

13. The diagnostic measuring device according to claim 1, wherein the hollow reflector comprises a chip housing that accommodates the at least one radiation source and the at least two radiation sensors within itself,
wherein the at least one radiation source and the at least two radiation sensors, in each instance, comprise at least one semiconductor body that:
is connected to conductor tracks that run in the interior of the chip housing and/or
comprises bond wire connections, and
wherein the chip housing has the first radiation exit and the second radiation exit on its top.

14. The diagnostic measuring device according to claim 13, wherein the at least one hollow reflector further comprises a transparent plastic material that fills the chip housing.

15. The diagnostic measuring device according to claim 13, wherein the chip housing has a passage opening on its top configured to receive the radiation scattered and/or transmitted by the body part.

16. The diagnostic measuring device according to claim 1, wherein the optic is configured to produce the first radiation beam as a directed emission.

17. The diagnostic measuring device according to claim 1, further comprising electrodes for EKG measurements.

18. The diagnostic measuring device according to claim 1, further comprising electrodes for bioelectric impedance measurements.

19. The diagnostic measuring device according to claim 1, further comprising
a housing comprising the at least one radiation source, the at least one hollow reflector, the first radiation exit, and the second radiation exit, and
at least one electrode disposed at or on a surface of said housing,
wherein the optical measuring unit is configured to emit the first radiation beam and the second radiation beam to the body part in a first body region or to detect the radiation scattered and/or transmitted from the body part in a first body region, and wherein said at least one electrode is configured to touch a skin surface in the first body region.

20. The diagnostic measuring device according to claim 1, wherein the at least one hollow reflector comprises an Ulbricht sphere.

21. The diagnostic measuring device according to claim 1, further comprising a computer programmed to determine at least one physiological parameter selected from the group consisting of:
- an arterial oxygen saturation,
- a venous oxygen saturation,
- a capillary oxygen saturation,
- a local oxygen consumption,
- a local glucose concentration,
- a glucose level,
- a heart rate,
- a fat content of the body tissue, and
- a water content of the body tissue.

22. A system comprising:
- a diagnostic measuring device for non-invasive determination of at least one physiological parameter, and
- a portable device or a portable accessory, the portable device or the portable accessory being connected to the diagnostic measuring device,
- wherein the diagnostic measuring device has an optical measuring unit comprising:
  - at least one radiation source for irradiating a body part of a patient,
  - at least two radiation sensors configured to detect radiation scattered and/or transmitted by the body part and configured to measure optical measurement values in the form of light intensities comprising transmitted intensity $I_T$ and/or intensities $I_{Rs1}$ and $I_{Rs2}$ that are scattered back from different tissue regions,
  - at least one hollow reflector, the at least one radiation source being disposed in the at least one hollow reflector,
  - a first radiation exit and a second radiation exit connected to the at least one hollow reflector, and
  - an optic configured to collect and emit radiation,
  - wherein the at least one radiation source emits radiation in the hollow reflector so that a diffusion level of the radiation in the hollow reflector is increased, so that diffused radiation is produced, and so that the diffused radiation is then conducted via the first radiation exit and via the second radiation exit,
  - wherein the first radiation exit comprises or is connected to the optic such that the optic is configured to collect the diffused radiation and to emit the diffused radiation as a first radiation beam at a first opening angle,
- wherein the second radiation exit is configured to emit the diffused radiation as a second radiation beam differently shaped from the first radiation beam and at a second opening angle,
- wherein the first radiation beam and the second radiation beam have different spatial characteristics and are configured to irradiate different volume ranges of the body part, and
- wherein the first opening angle is different from the second opening angle.

23. The system according to claim 22, wherein the portable device or the portable accessory is an entertainment device having communications technology and is a notebook, a laptop, a mobile telephone, a palmtop, or a handheld.

* * * * *